US010137301B2

(12) United States Patent
Apoux et al.

(10) Patent No.: US 10,137,301 B2
(45) Date of Patent: Nov. 27, 2018

(54) MULTI-CARRIER PROCESSING IN AUDITORY PROSTHETIC DEVICES

(71) Applicant: OHIO STATE INNOVATION FOUNDATION, Columbus, OH (US)

(72) Inventors: Frederic Christian Apoux, Columbus, OH (US); Eric William Healy, Dublin, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 274 days.

(21) Appl. No.: 14/774,458

(22) PCT Filed: Mar. 11, 2014

(86) PCT No.: PCT/US2014/023543
§ 371 (c)(1),
(2) Date: Sep. 10, 2015

(87) PCT Pub. No.: WO2014/164814
PCT Pub. Date: Oct. 9, 2014

(65) Prior Publication Data
US 2016/0022991 A1 Jan. 28, 2016

Related U.S. Application Data

(60) Provisional application No. 61/776,281, filed on Mar. 11, 2013.

(51) Int. Cl.
*A61N 1/36* (2006.01)
*A61N 1/05* (2006.01)
(Continued)

(52) U.S. Cl.
CPC ....... *A61N 1/36032* (2013.01); *A61N 1/0541* (2013.01); *A61N 1/36139* (2013.01);
(Continued)

(58) Field of Classification Search
CPC .............. A61N 1/0558; A61N 1/37235; A61N 1/3606; A61N 1/0512; A61N 1/37247;
(Continued)

(56) References Cited

U.S. PATENT DOCUMENTS

| 4,357,497 A | * 11/1982 | Hochmair | ............... A61F 11/04 |
| | | | 128/903 |
| 7,317,945 B2 | 1/2008 | Litvak et al. | |

(Continued)

FOREIGN PATENT DOCUMENTS

| WO | 2010/051857 A1 | 5/2010 |
| WO | 2010/057267 A1 | 5/2010 |

(Continued)

OTHER PUBLICATIONS

International Search Report and Written Opinion of the U.S. International Searching Authority from Application No. PCT/US2014/023543, dated Aug. 5, 2014.

(Continued)

*Primary Examiner* — Rex R Holmes
(74) *Attorney, Agent, or Firm* — Meunier Carlin & Curfman LLC

(57) ABSTRACT

A method for multi-carrier processing in an auditory prosthetic device comprises receiving an audio signal comprising multiple signals, each produced by an independent source, and identifying at least a first signal and a second signal in the received audio signal. The method also comprises adjusting an amplitude of a first carrier signal based on a first signal or a signal envelope associated with the first signal, and adjusting an amplitude of a second carrier signal based on a second signal or a signal envelope associated with the second signal. The amplitude-adjusted first and second signals are delivered to one or more stimulation devices associated with an auditory prosthetic.

20 Claims, 9 Drawing Sheets

(51) Int. Cl.
  *H04R 1/10* (2006.01)
  *H04R 25/00* (2006.01)
  *G10L 21/0364* (2013.01)
(52) U.S. Cl.
  CPC ...... *A61N 1/36192* (2013.01); *G10L 21/0364* (2013.01); *H04R 1/1083* (2013.01); *H04R 25/407* (2013.01); *H04R 2225/43* (2013.01); *H04R 2430/03* (2013.01)
(58) Field of Classification Search
  CPC .. A61N 1/05; A61N 1/36132; A61N 1/36146; A61N 1/36007; A61N 1/0551
  See application file for complete search history.

(56) References Cited

U.S. PATENT DOCUMENTS

| | | | |
|---|---|---|---|
| 8,280,087 B1 | 10/2012 | Bacon et al. | |
| 8,489,194 B2 | 7/2013 | Meister et al. | |
| 8,498,714 B2 | 7/2013 | Litvak et al. | |
| 2009/0312820 A1* | 12/2009 | Nie | A61N 1/36036 607/57 |
| 2012/0239385 A1* | 9/2012 | Hersbach | G10L 25/84 704/200.1 |
| 2013/0023967 A1* | 1/2013 | Stafford | A61N 5/0622 607/89 |

FOREIGN PATENT DOCUMENTS

| | | | | |
|---|---|---|---|---|
| WO | 2011/100802 A1 | 8/2011 | | |
| WO | WO 2011100802 A1 * | 8/2011 | ........... | H04R 25/606 |
| WO | WO 2012057267 A1 * | 5/2012 | ............... | B41N 1/24 |

OTHER PUBLICATIONS

Galvin III, J. J., & Fu, Q. J. (2005). Effects of stimulation rate, mode and level on modulation detection by cochlear implant users. Journal of the Association for Research in Otolaryngology, 6(3), 269-279.

Apoux, F., & Healy, E. W. (2013). A glimpsing account of the role of temporal fine structure information in speech recognition. Basic Aspects of Hearing (pp. 119-126). Springer New York.

Apoux, F., Yoho, S. E., Youngdahl, C. L., & Healy, E. W. (2013). Role and relative contribution of temporal envelope and fine structure cues in sentence recognition by normal-hearing listeners. The Journal of the Acoustical Society of America, 134(3), pp. 2205-2212.

Apoux, F., Youngdahl, C. L., Yoho, S. E., & Healy, E. W. (2015). Dual-carrier processing to convey temporal fine structure cues: Implications for cochlear implants. The Journal of the Acoustical Society of America, 138(3), pp. 1469-1480.

Deeks, J. M., & Carlyon, R. P. (2004). Simulations of cochlear implant hearing using filtered harmonic complexes: Implications for concurrent sound segregation. The Journal of the Acoustical Society of America, 115(4), pp. 1736-1746.

Duran, S. I., Collins, L. M., & Throckmorton, C. S. (2012). Stream segregation on a single electrode as a function of pulse rate in cochlear implant listeners. The Journal of the Acoustical Society of America, 132(6), pp. 3849-3855.

Gnansia, D., Pressnitzer, D., Péan, V., Meyer, B., & Lorenzi, C. (2010). Intelligibility of interrupted and interleaved speech for normal-hearing listeners and cochlear implantees. Hearing research, 265, pp. 46-53.

Kwon, B. J. (2009). Effects of electrode separation between speech and noise signals on consonant identification in cochlear implants. The Journal of the Acoustical Society of America, 126(6), pp. 3258-3267.

Lan, N., Nie, K. B., Gao, S. K., & Zeng, F.-G. (2004). A novel speech-processing strategy incorporating tonal information for cochlear implants. Biomedical Engineering, IEEE Transactions on, 51(5), pp. 752-760.

Li, X., Nie, K., Imennov, N. S., Won, J. H., Drennan, W. R., Rubinstein, J. T., & Atlas, L. E. (2012). Improved perception of speech in noise and Mandarin tones with acoustic simulations of harmonic coding for cochlear implants. The Journal of the Acoustical Society of America, 132(5), pp. 3387-3398.

Luo, X., & Fu, Q.-J. (2009). Concurrent-vowel and tone recognitions in acoustic and simulated electric hearing. The Journal of the Acoustical Society of America, 125(5), pp. 3223-3233.

Mc Laughlin, M., Reilly, R. B., & Zeng, F.-G. (2013). Rate and onset cues can improve cochlear implant synthetic vowel recognition in noise. The Journal of the Acoustical Society of America, 133(3), pp. 1546-1560.

Nie, K., Stickney, G., & Zeng, F.-G. (2005). Encoding frequency modulation to improve cochlear implant performance in noise. Biomedical Engineering, IEEE Transactions on, 52(1), pp. 64-73.

Riss, D., Arnoldner, C., Baumgartner, W.-D., Kaider, A., & Hamzavi, J.-S. (2008). A new fine structure speech coding strategy: speech perception at a reduced number of channels. Otology & Neurotology, 29(6), pp. 784-788.

Riss, D., Hamzavi, J.-S., Selberherr, A., Kaider, A., Blineder, M., Starlinger, V., Gstoettner, W., & Arnoldner, C. (2011). Envelope versus fine structure speech coding strategy: a crossover study. Otology & Neurotology, 32(7), pp. 1094-1101.

Shannon, R. V., Zeng, F.-G., Kamath, V., Wygonski, J., & Ekelid, M. (1995). Speech recognition with primarily temporal cues. Science, 270, pp. 303-304.

Stickney, G. S., Nie, K., & Zeng, F.-G. (2005). Contribution of frequency modulation to speech recognition in noise. The Journal of the Acoustical Society of America, 118(4), pp. 2412-2420.

Stickney, G. S., Assmann, P. F., Chang, J., & Zeng, F.-G. (2007). Effects of cochlear implant processing and fundamental frequency on the intelligibility of competing sentences. The Journal of the Acoustical Society of America, 122(2), pp. 1069-1078.

Stohl, J. S., Throckmorton, C. S., & Collins, L. M. (2008). Assessing the pitch structure associated with multiple rates and places for cochlear implant users. The Journal of the Acoustical Society of America, 123(2), pp. 1043-1053.

Stohl, J. S., Throckmorton, C. S., & Collins, L. M. (2009). Investigating the effects of stimulus duration and context on pitch perception by cochlear implant users. The Journal of the Acoustical Society of America, 126(1), pp. 318-326.

Throckmorton, C. S., Kucukoglu, M. S., Remus, J. J., & Collins, L. M. (2006). Acoustic model investigation of a multiple carrier frequency algorithm for encoding fine frequency structure: Implications for cochlear implants. Hearing Research, 218, pp. 30-42.

Wilson, B. S., Finley, C. C., Lawson, D. T., Wolford, R. D., Eddington, D. K., & Rabinowitz, W. M. (1991). Better speech recognition with cochlear implants. Nature, 352, pp. 236-238.

Wilson, B. S., Finley, C. C., Lawson, D. T., Wolford, R. D., & Zerbi, M. (1993). Design and evaluation of a continuous interleaved sampling (CIS) processing strategy for multichannel cochlear implants. Journal of Rehabilitation Research and Development, 30(1), pp. 110-116.

Zeng, F.-G., Nie, K., Stickney, G. S., Kong, Y. Y., Vongphoe, M., Bhargave, A., Wei, C., & Cao, K. (2005). Speech recognition with amplitude and frequency modulations. Proceedings of the National Academy of Sciences of the United States of America, 102(7), pp. 2293-2298.

Extended European Search Report issued by the European Patent Office in Application No. 14778588.5, dated Nov. 8, 2016, 7 pages.

European Patent Office Communication Pursuant to Article 94(3) EPC issued in European Application No. 14778588.5 dated Mar. 13, 2018 (3 pages).

* cited by examiner

MULTI-CARRIER PROCESSING IN AUDITORY PROSTHETIC DEVICES

CROSS-REFERENCE TO RELATED APPLICATION

This application claims the benefit of U.S. Provisional Application No. 61/776,281, filed Mar. 11, 2013, which is incorporated herein by reference in its entirety.

TECHNICAL FIELD

The present disclosure relates generally to cochlear implants and other auditory aids and, more particularly, to systems and methods for delivering temporal fine structure cues in cochlear implants using multi-carrier processing.

BACKGROUND

Sounds can be described as the sum of band-limited signals, each of which corresponding to the product of an envelope (the slow amplitude fluctuations) and a fine structure (the rapid fluctuations in amplitude close to the center frequency of the signal). In everyday life, our acoustic environment is generally composed of more than one sound, each produced by an independent source. Processing the information corresponding to a particular source often requires isolating one sound from the mixture of sounds. Further, full analysis of the auditory scene involves monitoring and awareness of the multitude of sound sources in the environment. The auditory system of a human with normal hearing function is reasonably effective in extracting a sound from a mixture. For instance, when several persons are talking simultaneously, the auditory system is able to "tune in" to a single voice and "tune out" all others. The auditory system of a human with normal hearing function is also reasonably effective at maintaining an awareness of multiple sound sources and switching attention between these sources, should that become necessary. Studies suggest that temporal fine structure (TFS) cues play an important role in extracting the desired audio signal from a mixture of sounds, especially when the background is fluctuating in frequency and/or time.

There are currently a number of prosthetic devices, such as cochlear implants, that seek to restore hearing in the profoundly deaf by stimulating the auditory nervous system via electrodes inserted into the auditory system. Most cochlear-implant users have great difficulties understanding speech in noise. Complicating the issue is the fact that cochlear-implant processors replace the temporal fine structure (or carrier) of the incoming sounds with a single pulse train, limiting the availability of temporal fine structure cues to the auditory system to segregate sound sources.

To circumvent this limitation, conventional cochlear-implant processors may attempt to suppress all but one sound source (the desired or "target" speech signal), thereby allowing users to process at least one signal effectively. There are several drawbacks to this approach. First, this approach assumes that the noise reduction system knows which signal is the target signal. If the user wishes to listen to an audio signal other than the one that the system selected as the target, the user would be unable to do so. Furthermore, this approach may have limited effectiveness in situations where the acoustic environment is less than ideal (i.e., situations in which the target signal is not easy to identify).

An alternative approach currently employed by cochlear implants is to convey all sounds in the environment, but to convey all these sounds on a single carrier. This carrier often consists of a pulse train having a single pulse rate. Such approach generally results in poor speech intelligibility.

Another limitation of conventional cochlear implants is that most are designed primarily to extract and transmit temporal envelope information to the user, discarding TFS information. As noted above, however, TFS information has been shown to play a significant role in extracting an audio signal from among other signals.

There have been a few attempts to provide the original TFS from the target speech to cochlear-implant users. Providing the original fine structure to cochlear-implant users, however, is technically challenging and as a result, most approaches transmit fine structure related cues in only limited fashion. Although these approaches may provide some benefit, the improvement in speech recognition remains limited.

The presently disclosed systems and methods for multi-carrier processing for auditory prosthetic devices are directed toward overcoming one or more of the problems set forth above and/or other problems in the art.

SUMMARY

According to one aspect, the present disclosure is directed toward a method for multi-carrier processing in an auditory prosthetic device. The method involves receiving an audio signal composed of multiple signals, each produced by an independent source and identifying at least a first signal in the received audio signal. The method also involves dynamically adjusting an amplitude associated with a first carrier based on the identified first signal and dynamically adjusting an amplitude associated with a second carrier based on a second signal contained in the audio signal. The method may also involve delivering the modulated first and second signals to electrodes or other stimulation devices (e.g., laser diodes, LEDs, or other devices for administering or emitting optical, IR, UV, or other types of stimulation) associated with a cochlear implant or other auditory prosthetic. It should be noted that the term "electrode" and "stimulator" are used interchangeably for the purposes of description.

In accordance with another aspect, the present disclosure is directed toward a processor-implemented method for delivering temporal fine structure information in addition to any other signal-related information to an output of an auditory prosthetic device. The method involves receiving an audio signal composed of multiple signals, each produced by an independent source and identifying at least a first signal and a second signal in the received audio signal. The method also involves estimating a fundamental frequency of the first signal and estimating a fundamental frequency of the second signal. The amplitude of a first carrier may be dynamically adjusted according to the amplitude or temporal envelope of the first signal, wherein the frequency of the first carrier is determined according to the fundamental frequency of the first signal. The amplitude of a second carrier may be dynamically adjusted according to the amplitude or temporal envelope of the second signal, wherein the frequency of the second carrier is determined according to the fundamental frequency of the second signal. The modulated first and second signals may be delivered to an electrode associated with a cochlear implant or other auditory prosthetic.

According to another aspect, the present disclosure is directed toward an auditory prosthetic device. The auditory prosthetic device may be composed of a microphone for detecting an audio signal, an electrode(s) adapted for implantation proximate to an auditory nerve or other neural structure of a patient and configured to deliver stimulation to the nerve or structure, and a processor communicatively coupled to the microphone and the electrode(s). The processor may be configured to identify at least a first signal in the detected audio signal. The processor may also be configured to modulate a first carrier frequency based on the first signal and modulate a second carrier frequency based on the remaining signals. The processor may be further configured to deliver the modulated first and second signals to the electrode(s).

DETAILED DESCRIPTION

Figure 1:
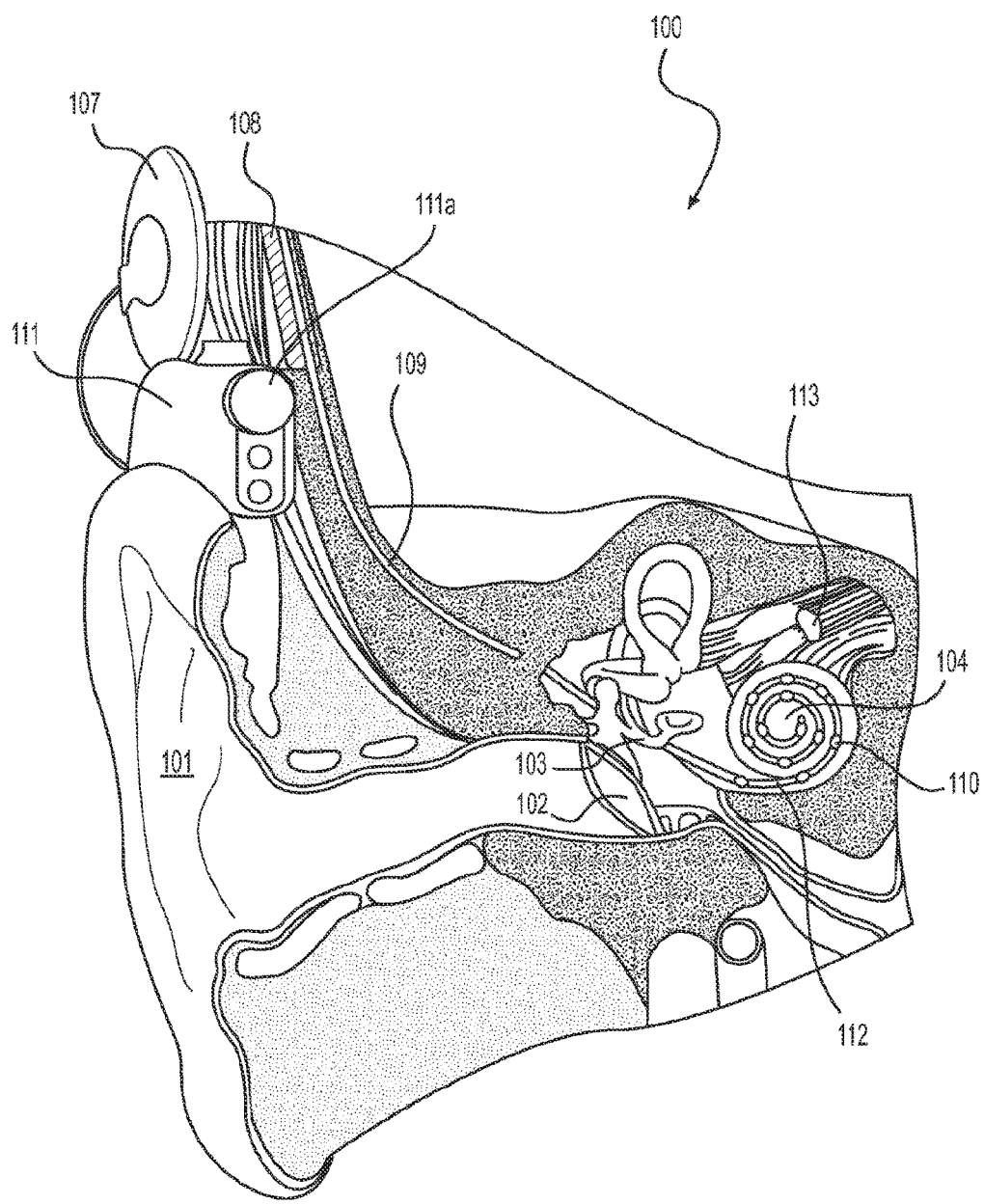
FIG. 1 provides a diagrammatic view of an exemplary application environment of an auditory prosthetic device, in accordance with the disclosed embodiments.

FIG. 1 illustrates an exemplary application environment 100 for an auditory prosthetic device, such as a cochlear implant. As illustrated in FIG. 1, the auditory prosthetic device may include, among other things, a processing module 111 including a microphone 111a, a transmitting coil 107, an internal receiver/stimulator 108, an electrode lead, and an electrode array 112 comprising one or more electrode contacts 110. According to an exemplary embodiment, the microphone 111a provides an audio signal input to the processing module 111, which implements various signal processing schemes (like A/D conversion, noise reduction, and signal separation, among others), such as the multi-carrier processing scheme which will be described in more detail hereinafter. The processed signal is formatted for transmission by the transmitting coil 107 and the internal receiver/stimulator 108. The receiver processor in the internal receiver/stimulator 108 receives the digital data and delivers it through an electrode lead 109 to an implanted electrode array 112 which penetrates into the cochlea 104 through a surgical opening called a cochleostomy. Typically, this electrode array 112 includes multiple electrode contacts 110 on its surface that deliver the stimulation signals to adjacent neural tissue of the cochlea 104, which the brain of the patient interprets as sound. The individual electrode contacts 110 or other stimulator devices may be activated in any of a number of schemes (e.g., sequentially, non-sequentially, simultaneously, etc.) in one or more contact groups, depending upon the design scheme of the cochlear implant.

Processes and methods consistent with the disclosed multi-carrier processing schemes are aimed at placing the user at the center of the noise reduction process. For example, rather than attempting to extract the target signal and/or the original envelope and temporal fine structure (TFS) data (and suppressing all other data), systems and methods consistent with the disclosed embodiments are directed toward providing a mixture of signals from different sound sources (i.e., both target signal and background signal(s)) on separate carriers, each having a particular rate or frequency, thereby allowing the user's auditory system to naturally exploit the TFS differences to determine the desired signal to listen to.

Because fine structure information may be primarily involved in source segregation (rather than source identification), artificial but perceptually relevant differences between the carriers used to transmit the target and the background signals may be sufficient to support effective segregation and therefore substantially improve speech recognition in noise by users of cochlear-implants and other auditory prosthetics. Furthermore, introducing small pitch differences by using independent carriers for the target and the background envelopes may enhance a user's ability to differentiate between target and background signals.

Figure 2:
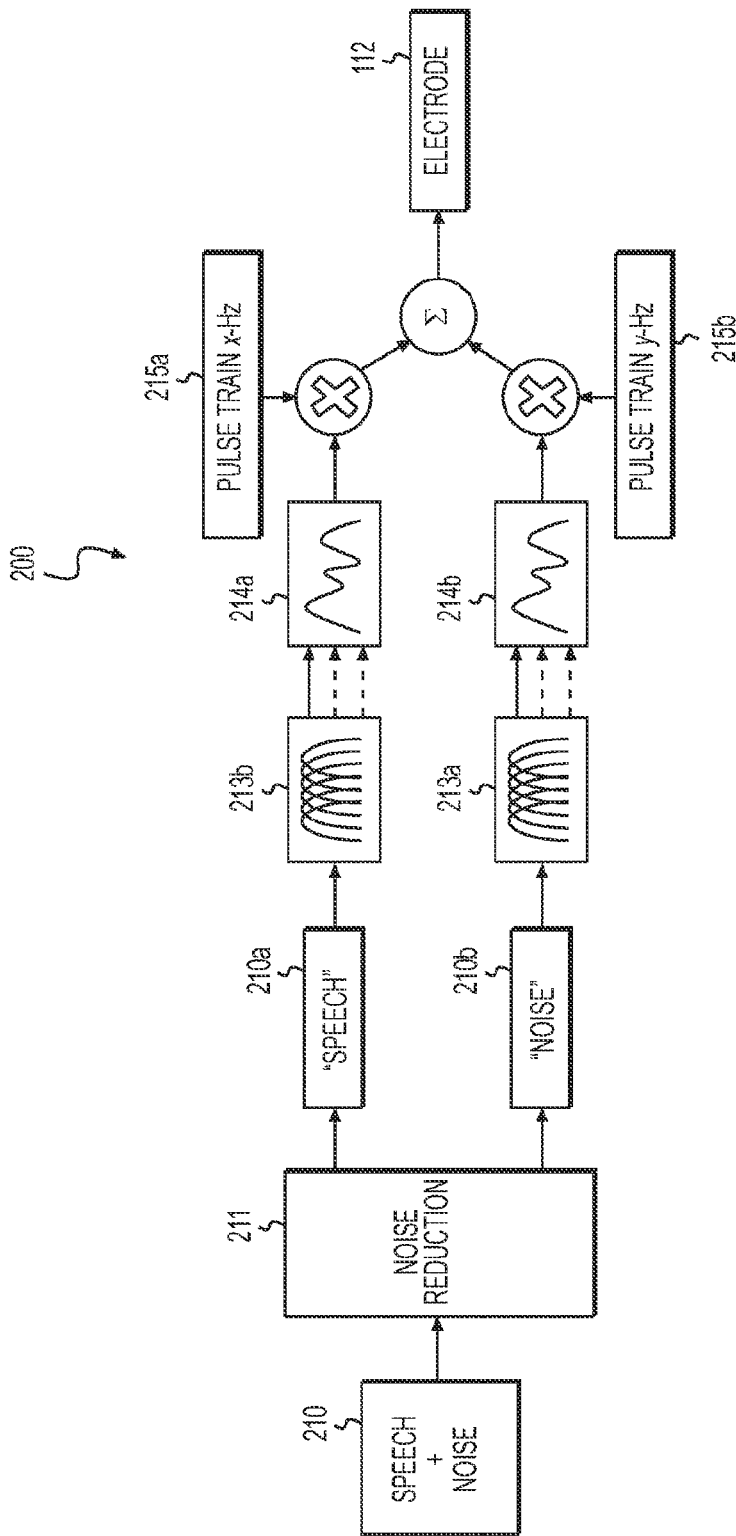
FIG. 2 provides a block diagram associated with a multi-carrier processing scheme that can be implemented in an auditory prosthetic device, consistent with the disclosed embodiments.
Figure 3:
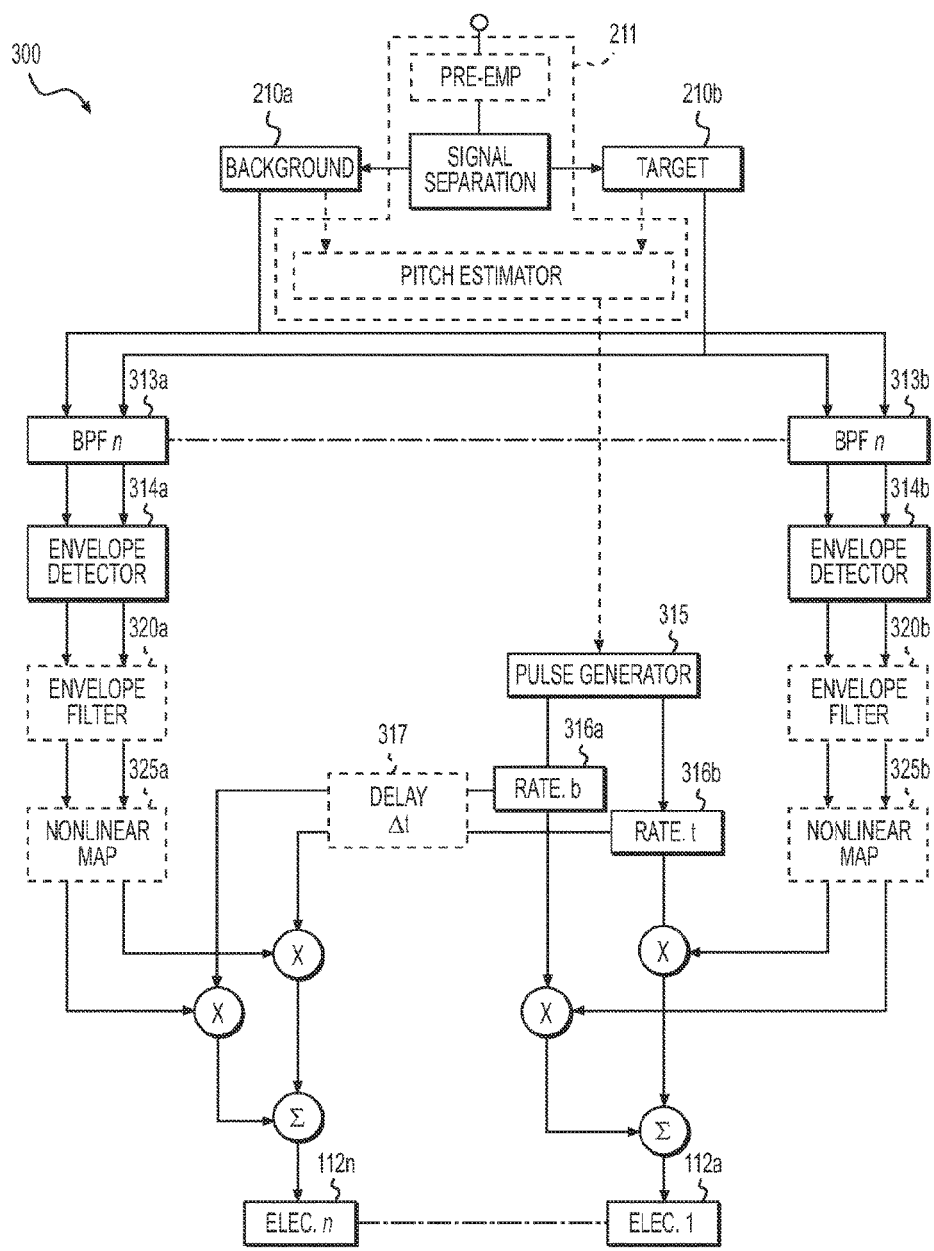
FIG. 3 provides a schematic illustrating certain exemplary components associated with a multi-carrier processing system, in accordance with certain disclosed embodiments.

FIGS. 2 and 3 provide a functional block diagram 200 and exemplary schematic diagram 300, respectively, associated with a multi-carrier processing scheme that can be implemented in an auditory prosthetic device, consistent with certain disclosed embodiments. As illustrated in FIG. 2, an audio signal 210 composed of a speech signal embedded in background noise(s) 210 may be received/detected by a microphone 111a and pre-processed at block 211 using conventional noise reduction and signal separation techniques.

At blocks 213a, 213b, the resulting speech signal 210a and noise signal 210b may each be divided into complementary spectral bands or channels wherein each channel is designed to pass only a relatively narrow selected band of frequencies around some center frequency. According to one embodiment, the spectral band separation may be performed using a bank of band-pass filters or a Fourier analysis, effectively dividing each signal into a plurality of complementary frequency bands or channels spanning the desired range. By proper selection of filter channel frequencies, the channels may encompass all or a large part of the audio frequency spectrum relevant for speech (e.g., 80-7,562 Hz).

Once each of the speech and background signals have been divided, each frequency channel of the speech and background signal may undergo envelope detection and/or compression at blocks 214a, 214b. According to one embodiment, the envelope detectors may include or embody a full-wave or half-wave rectifier. According to another exemplary embodiment, a Hilbert transform may also be used. The bandwidth of the envelope in each channel may further be limited by implementing a low-pass filter (not shown).

Once the narrow-band envelopes are obtained at blocks 214a, 214b, two independent pulse trains may be amplitude-adjusted (e.g., multiplied, amplitude modulated, etc.) based on the narrow-band envelopes obtained in each channel. According to one embodiment, the rate of the pulse train conveying the target envelope (block 215a) is set to 150, 250 or 350 Hz while the rate of the pulse train conveying the background or noise envelope (block 215b) may be selected from 100 to 350 Hz in 50 Hz steps. The amplitude-adjusted pulse trains are finally summed over all channels to produce the dual-carrier stimulus, which is applied to electrode array 112 for delivery to the auditory nerve of the user. The resulting stimuli applied to each electrode may include a sound mixture that is made up of two amplitude adjusted pulse trains whose rate may differ by as few as 0 (i.e., single-carrier condition) and as much as 250 Hz.

FIG. 3 provides a schematic illustrating certain exemplary components associated with a multi-carrier processing system, in accordance with certain disclosed embodiments. As illustrated in FIG. 3, the incoming audio signal undergoes analog-to-digital conversion. The input can be provided by a microphone or other sources. Following the input, a signal separation module 211 (including a pre-emphasis filter, a noise reduction/signal separation module, and a pitch estimator) may process the incoming audio signal. The pre-emphasis filter may be used to attenuate strong components in speech below a predetermined frequency. According to one embodiment, this predetermined frequency may include about 1.2 kHz. Following this initial filtering step, the signal of interest (i.e., the target signal) 210b is isolated and extracted from the digitized sound mixture using noise reduction or signal separation. These techniques may include or embody any device or process able to separate audio signals, including existing noise reduction/signal separation techniques such as multi-microphone techniques (e.g., beamforming) or single-microphone noise-reduction or speech-enhancement algorithms.

According to one embodiment, the background signal 210a may be subsequently derived, for example, by inverting the target signal waveform and subtracting the resulting amplitude-inversed signal from the digitized sound mixture. According to one embodiment, additional and/or constituent sound sources comprising the background signal can also be estimated and isolated. Each additional sound source typically requires a corresponding additional carrier for conveying the additional sound source separately to the user. It is contemplated, however, that the presently disclosed embodiments may be directed to situations involving one carrier for the target signal and one carrier for the background signal (i.e., a dual-carrier implementation).

According to one embodiment, the pre-processing stage (e.g., the signal separation module) may include a pitch estimator. The pitch estimator may include or embody any device or process suitable for estimating a fundamental frequency of the target signal and the background signal. The fundamental frequencies of each signal may be provided to the pulse generator 315, and used to adjust the rate of the train of pulses used to convey each amplitude envelope signals to the user. Using the fundamental frequency, although optional, aids in providing a "natural" experience to the user of the cochlear implant or other auditory prosthetic device.

In one embodiment, the target and the background signals are each divided into 22 complementary spectral bands or channels wherein each channel is designed to pass only a relatively narrow selected band of frequencies around some center frequency. According to one embodiment, the spectral band separation may be performed using a bank of band-pass filters 313a, 313b or a Fourier analysis, effectively dividing each signal into a plurality of complementary frequency bands or channels. By proper selection of filter channel frequencies, the channels may encompass all or a large part of the audio frequency spectrum.

According to an exemplary embodiment, noise reduction/signal separation may be implemented before or after sub-band division. The specific order is not believed to influence the benefit of the process. Implementing noise reduction after band division, however, may result in longer processing time and reduce autonomy.

Once the signals have been band-divided, each channel may undergo one or more stages of envelope detection and compression. According to one embodiment, the envelope detectors 314a, 314b typically use a full- or half-wave rectifier. According to another embodiment, envelope detectors 314a, 314b may include or embody a device for implementing Hilbert transform. Optionally, the bandwidth of the envelope in each channel may further be limited by implementing a low-pass filtering 320a, 320b.

According to one embodiment, at least two trains of pulses are generated for each channel. The rate of the train of pulses differ from one another by at least about 20 Hz to allow the user to perceive two signals. One set of train of pulses (RATE.t, denoted as reference numeral 316b) is multiplied or amplitude-modulated by the target envelopes and the other set (RATE.b, denoted as reference numeral 316a) is multiplied or amplitude-modulated by the background envelopes. Optionally, the amplitude of the trains of pulses can be amplitude adjusted in non-linear fashion using non-linear maps 325a, 325b applied to the respective background and target envelope signals.

In an alternate embodiment, a single train of pulses (RATE.t*b, not shown) corresponding to the arithmetic product of the rate selected to convey the target envelopes (RATE.t) and that selected to convey the background envelopes (RATE.b) is generated for each channel. The amplitude of each individual pulse is then made proportional to the corresponding time segment of the target envelope, the background envelope, the summed target and background envelopes, or set to zero or a noise floor value to provide the illusion of two amplitude adjusted train of pulses. Optionally, the amplitude of the trains of pulses can be amplitude adjusted in non-linear fashion using non-linear maps 325a, 325b applied to the respective background and target envelope signals.

According to one embodiment, the resulting amplitude-modulated train of pulses in each channel is directed to at least one intra-cochlear electrodes (or other type of stimulators) through a radio-frequency link, with low-to-high frequency channels assigned to apical-to-basal electrodes, to mimic at least the order, if not the precise locations, of frequency mapping in the normal cochlea.

In some embodiments, the pulse trains for the different channels and corresponding electrodes are delivered to the electrodes in an interleaved or non-overlapping fashion (e.g., by applying a respective predetermined delay 317 at the input of the different electrodes) to minimize electrical field interactions between stimulated electrodes. In other words, the pulses across channels and electrodes are non-simultaneous.

Figure 4:
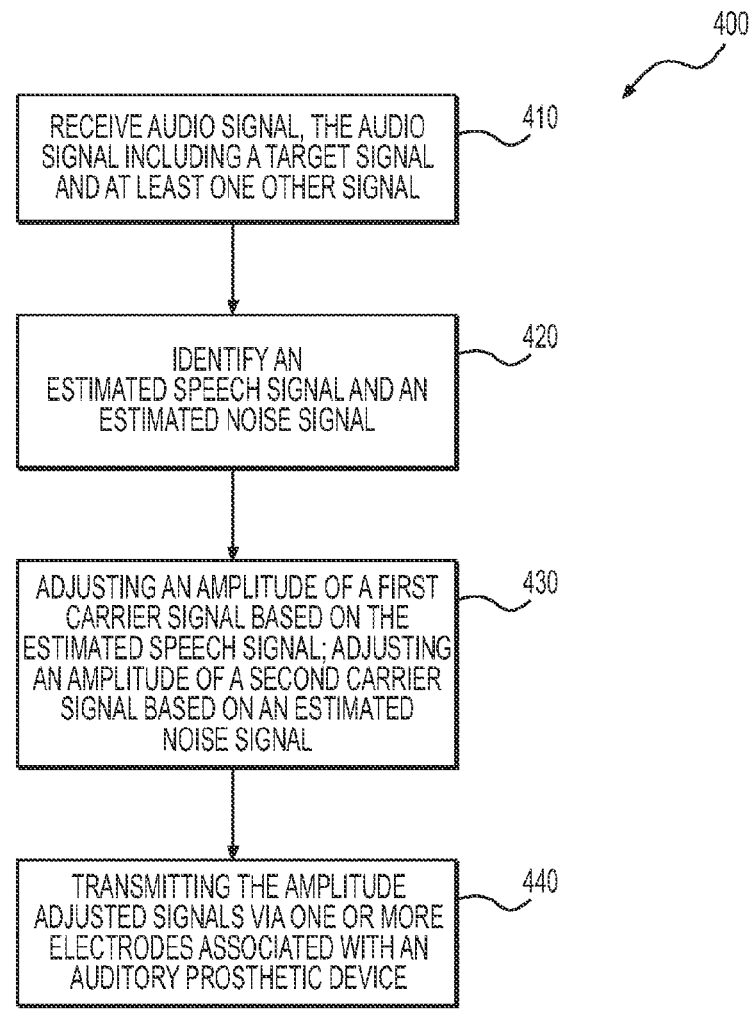
FIG. 4 provides a flowchart depicting an exemplary process for multi-carrier processing of audio signals, consistent with certain disclosed embodiments.

Processes and methods consistent with the disclosed embodiments provide a solution for enhancing target detection in cochlear implant users by using a multi-carrier approach for delivering both target and background signals to the implant electrode array, thereby replicating temporal fine structure cues that have been shown to be important to aiding users in differentiating between target and background signals. FIG. 4 provides a flowchart 400 illustrating an exemplary process that may be performed by a signal processing system of a cochlear implant or other neural prosthesis to extract and deliver the target signal and background signals on different carrier frequencies.

As illustrated in flowchart 400 of FIG. 4, the processes commences upon receipt of an audio signal (Block 410). The audio signal may include a target signal (such as speech, for example) and at least one other signal (such as background noise, for example). As explained, audio signals may be detected by a microphone 111a of a cochlear implant and delivered to the input of signal processing stage for processing and eventual delivery to a user of the system.

As part of the processing stage, the audio signal may undergo "preliminary" signal processing in order to remove spectral components outside of the audible frequency range that is typically associated with speech and to attenuate strong components in speech below a predetermined frequency, such as 1.2 kHz (pre-emphasis filter).

Once the target signal has been identified, the background signal may be subsequently derived, for example, by inverting the target signal waveform and subtracting the resulting amplitude-inversed signal from the digitized sound mixture. According to one embodiment, additional and/or constituent sound sources of the background signal can also be estimated and isolated. Each additional sound source typically requires a corresponding additional carrier for conveying the additional sound source separately to the user. It is contemplated, however, that the presently disclosed embodiments may be directed to situations involving one carrier for the target signal and one carrier for the background signal (i.e., a dual-carrier implementation).

Once the target signal and any background signals have been estimated, a respective carrier may be selected and modulated in amplitude based on each of the target and background signals (Block 440). In other words, the amplitude of a first carrier signal may be adjusted dynamically based on a target signal and the amplitude of a second carrier signal may be adjusted dynamically based on any background signals, each carrier signal having a different rate or frequency. According to one embodiment, the pre-processing stage includes a pitch estimator for estimating a fundamental frequency of the target signal and the background signal. The fundamental frequencies of each signal may be provided to the carrier generator, and used to adjust the carrier frequency of the amplitude-modulated signals delivered to the user. Using the fundamental frequency, although optional, aids in providing a "natural" experience to the user of the cochlear implant.

Each of the amplitude-modulated signals may be delivered to an electrode array for stimulation of the auditory nerve of a user (Block 450). According to one embodiment, the amplitude-modulated signals in each channel may be directed to at least one intra-cochlear electrode (or any other stimulator (e.g., optical, IR, UV, etc.) through a radio-frequency link, with low-to-high frequency channels assigned to apical-to-basal electrodes, to mimic at least the order, if not the precise locations, of frequency mapping in the normal cochlea. Alternatively or additionally, the pulse trains for the different channels and corresponding electrodes are delivered to the electrodes in an interleaved or non-overlapping fashion (e.g., by applying a respective predetermined delay 317 at the input of the different electrodes) to minimize electrical field interactions between stimulated electrodes.

FIG. 3 shows the diagram of a preferred "dual-carrier" embodiment. The dashed arrows and boxes designate optional process. The input, indicated by filled circle at the top of diagram, is a digitized audio signal. After a pre-emphasis stage, it is decomposed into two signals, a target and a background. If desired, pitch can be approximated for each signal and subsequently used to adjust the rate of the target and background carriers. The decomposition stage is followed by multiple-channel processing. Each channel includes stages of band-pass filtering, envelope detection, and optional low-pass filtering and non-linear mapping. These stages are applied separately to the estimated target and background signals. The resulting target and background narrow-band envelopes are then used to adjust dynamically the amplitude of a pulse train; one for the target envelope and one for the background envelope in each channel. The target and background amplitude-adjusted pulse trains are summed at the output of each channel and directed to the corresponding intracochlear electrode.

Figure 5:
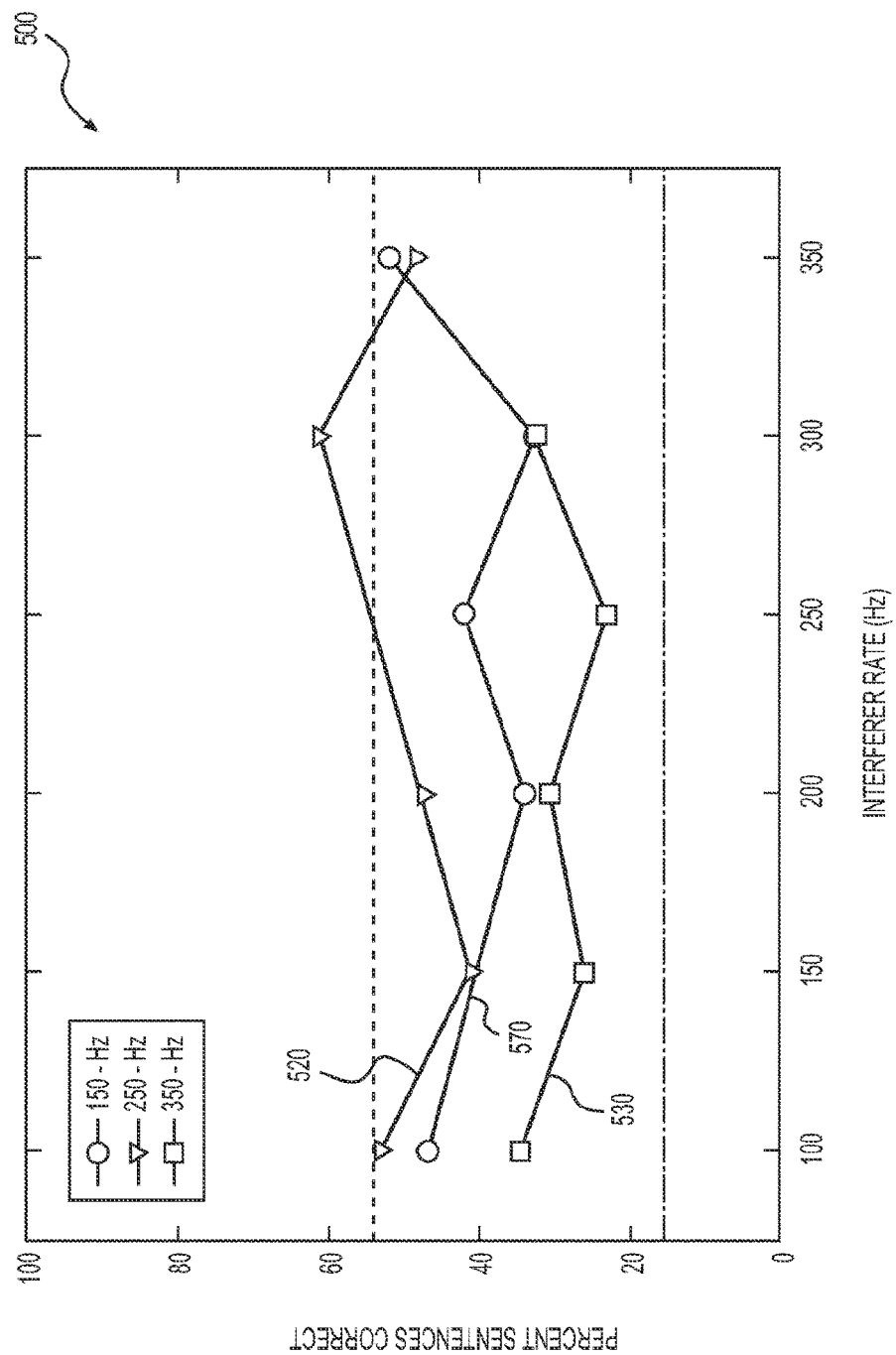
FIG. 5 provides data from normal-hearing subjects showing percentage of words understood when listening to a cochlear implant simulation that implements the presently-disclosed multi-carrier processing scheme as a function of the carrier frequency that is used to convey the background signal (a speech-shaped noise). The carrier frequency that is used to convey the target signal is the parameter.
Figure 6:
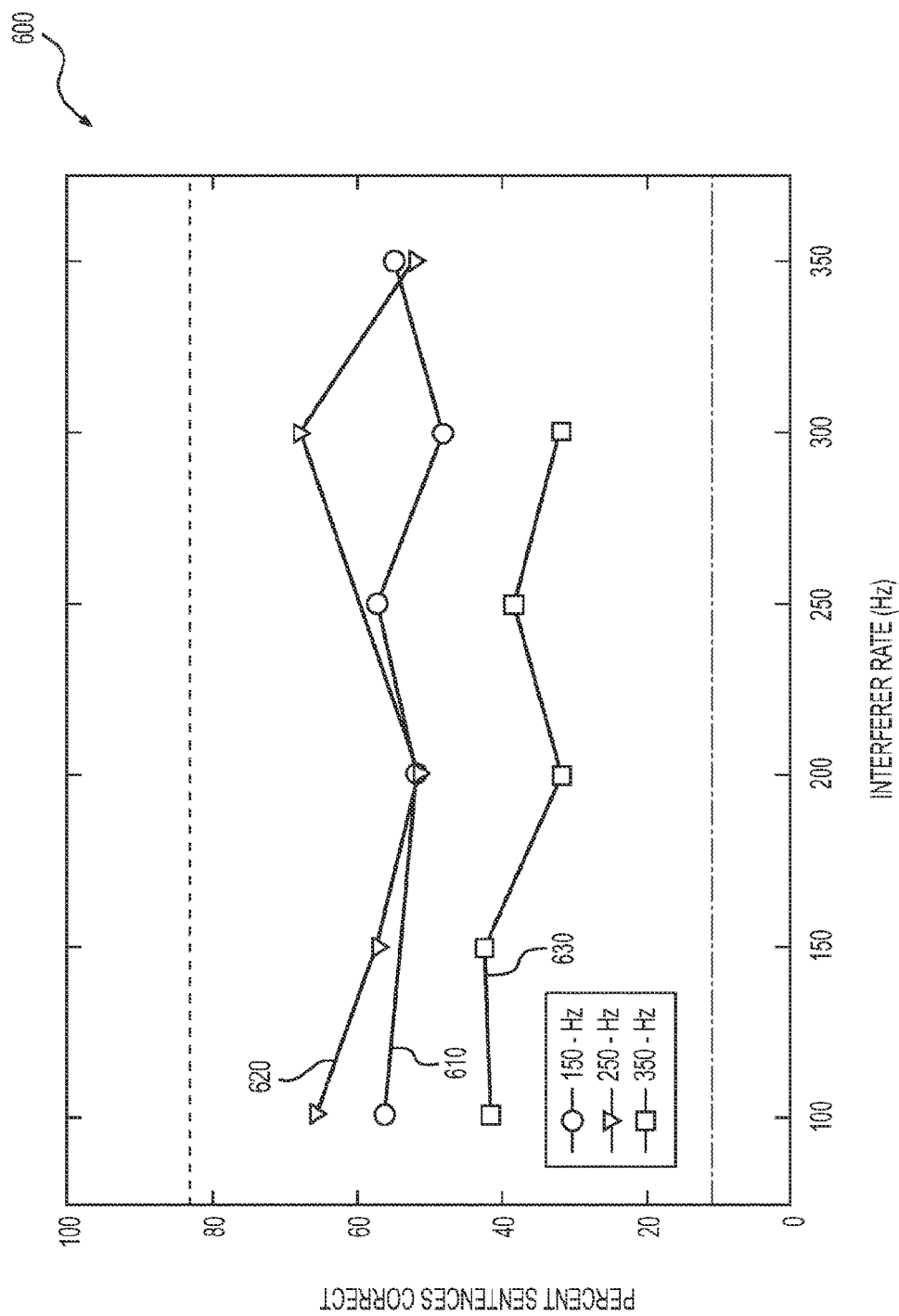
FIG. 6 provides data from normal-hearing subjects showing percentage of words understood when listening to a cochlear implant simulation that implements the presently-disclosed multi-carrier processing scheme as a function of the carrier frequency that is used to convey the background signal (a single talker voice played backward). The carrier frequency that is used to convey the target signal is the parameter.
Figure 7:
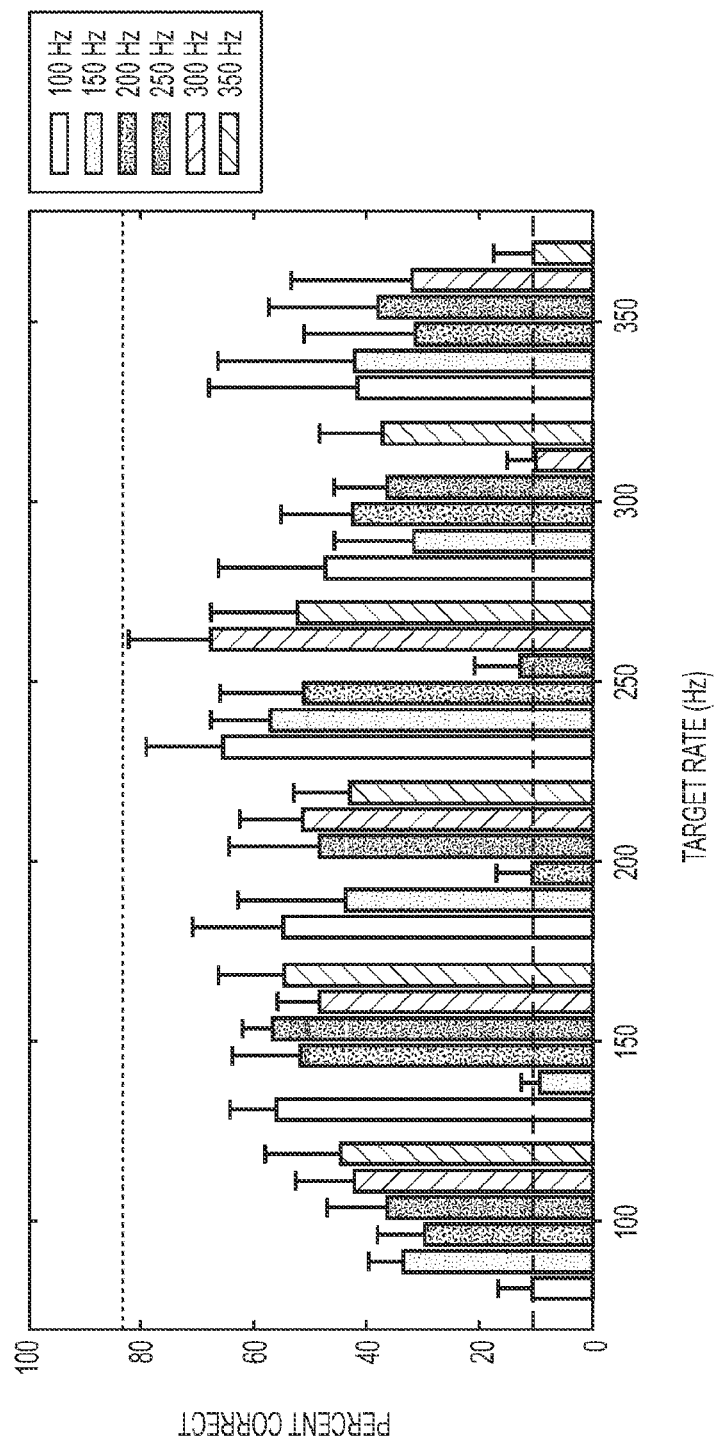
FIG. 7 provides another representation of the normal-hearing data showing percentage of words understood when listening to a cochlear implant simulation that implements the presently-disclosed multi-carrier processing scheme as a function of the carrier frequency that is used to convey the target signal. The carrier frequency that is used to convey the background is the parameter.

FIGS. 5, 6, and 7 present data from a simulated operation of a cochlear implant using the multi-carrier processing scheme disclosed herein. FIGS. 5 and 6 represent data from two separate tests conducted on different normal-hearing subjects listening to a cochlear implant simulation implementing the multi-carrier processing system. The primary difference between FIGS. 5 and 6 is the use of a speech-shaped noise and a single talker voice played backward as background, respectively. FIGS. 5 and 6 illustrate the percentage of words correctly identified as a function of the carrier frequency used to convey the background sound (RATE.b). The parameter is the rate used to convey the target sound (RATE.t). The dashed-dotted line indicates the percentage of words correctly identified when using only one carrier to convey both the target and the background signals simultaneously. The dashed line indicates the percentage of words correctly identified by normal-hearing subjects when presented acoustically with the unprocessed stimuli. These data demonstrate the potential of the invention and suggest that speech intelligibility in noise by CI users could be restored to a level comparable to that of normal-hearing listeners while preserving the complexity of the acoustic environment. FIG. 7 illustrates the percentage of words correctly identified as a function of the carrier frequency used to convey the target sound (RATE.t). The parameter is the rate used to convey the background sound (RATE.b). The long-dash line indicates the percentage of words correctly identified when using only one carrier to convey both the target and the background signals simultaneously. The short-dash line indicates the percentage of words correctly identified by normal-hearing subjects when presented acoustically with the unprocessed stimuli. Data in FIG. 7 demonstrates the potential of the invention for a larger number of target and background rates when the background is a single talker voice played backward.

Figure 8:
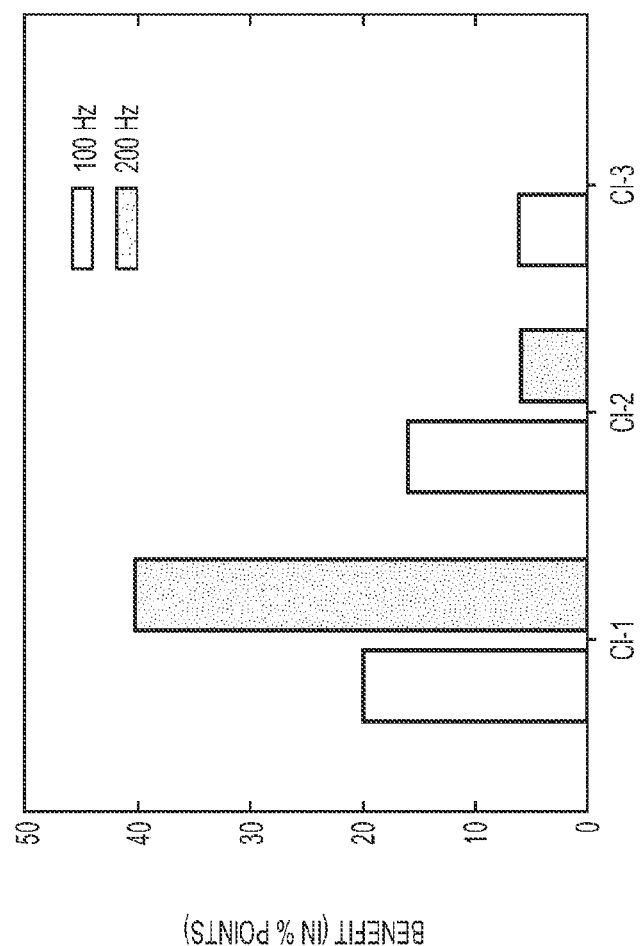
FIG. 8 shows the benefit of dual-carrier processing relative to the traditional single-carrier processing in percentage points for each of three cochlear-implant users. The carrier frequency that is used to convey the background is the parameter.

FIG. 8 illustrates data for three actual cochlear-implant users employing the multi-carrier processing system. This figure shows the benefit of dual-carrier processing in percentage points for each user relative to traditional single-carrier processing in which target and background are carried together on a single pulse train. The carrier frequency for the target signal (RATE.t) was set to 150 Hz. The parameter is the background rate (RATE.b).

Figure 9:
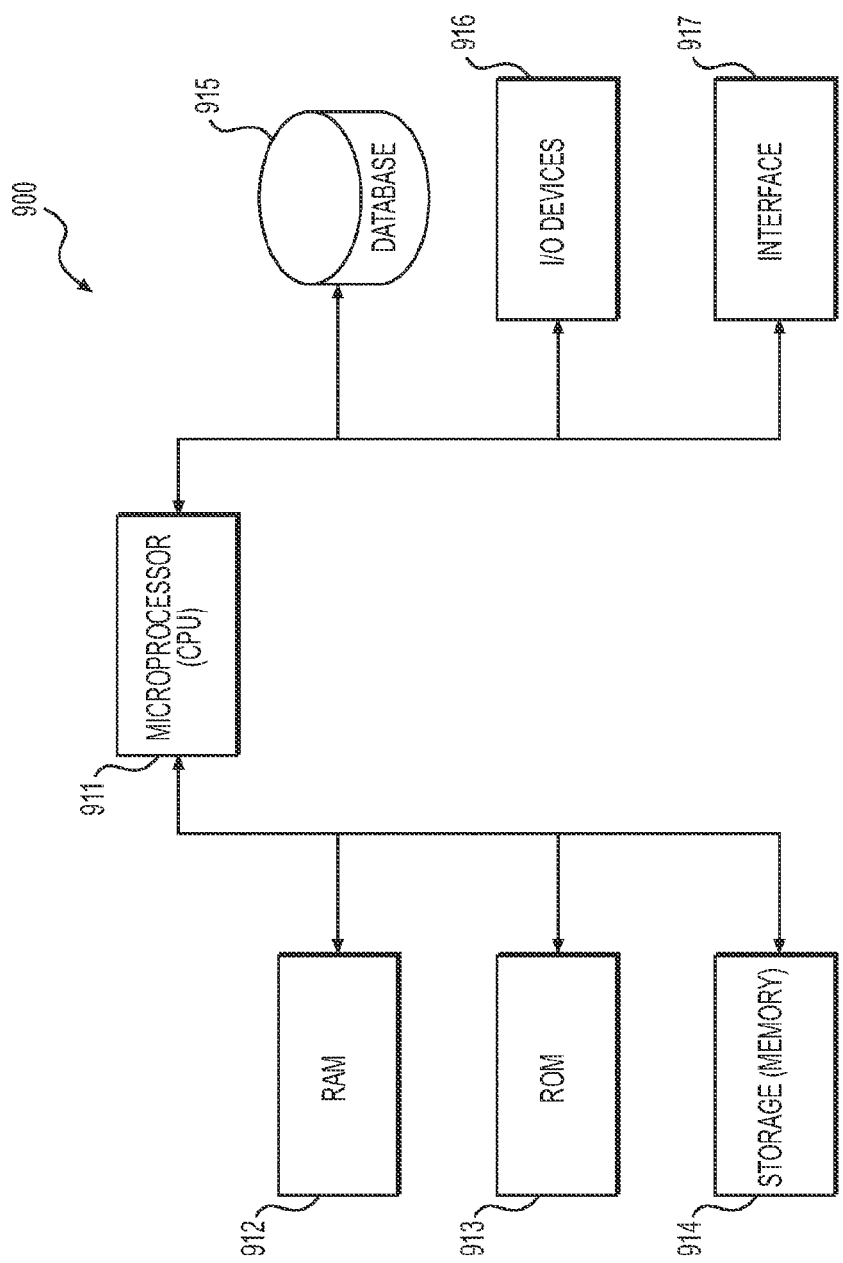
FIG. 9 provides a block diagram illustrating certain exemplary components associated with the processor-based computing device, in which various processing schemes, such as the multi-carrier processing scheme consistent with the disclosed embodiments, may be implemented.

One or more of processes and features associated with multi-carrier processing may be performed by dedicated application-specific integrated circuits (ASICs) and/or using general purpose processors executing signal processing software instructions. FIG. 9 illustrates an exemplary processor-based computing environment 800, one or more of which may be configured to execute signal processing software instructions, such as a multi-carrier processing scheme described in accordance with the disclosed embodiments. It should be noted that the components described with respect to FIG. 9 are exemplary only, and not intended to be limiting. For example, although FIG. 9 is illustrated as containing many components associated with a general purpose computer (e.g., database, internal storage, I/O devices, and network interfaces), it is contemplated that the presently disclosed multi-carrier processing scheme may be implemented by an ASIC and/or other microprocessor devices, without necessarily requiring all of the components shown in FIG. 9 (e.g., database, network interface, etc.)

As illustrated in FIG. 9, processing system 810 may include one or more hardware and/or software components configured to execute software programs, such as software for performing digital signal processing functions, such as the presently disclosed multi-carrier processing, for audio signals in cochlear implants or other auditory prosthetics. According to one embodiment, processing system 810 may include one or more hardware components such as, for example, a central processing unit (CPU) or microprocessor 811, a random access memory (RAM) module 812, a read-only memory (ROM) module 813, a memory or data storage module 814, a database 815, one or more input/output (I/O) devices 816, and an interface 817. Alternatively and/or additionally, processing system 810 may include one or more software media components such as, for example, a computer-readable medium including computer-executable instructions for performing methods consistent with certain disclosed embodiments. It is contemplated that one or more of the hardware components listed above may be implemented using software. For example, storage 814 may include a software partition associated with one or more other hardware components of processing system 810. Processing system 810 may include additional, fewer, and/or different components than those listed above. It is understood that the components listed above are exemplary only and not intended to be limiting.

CPU 811 may include one or more processors, each configured to execute instructions and process data to perform one or more functions associated with processing system 810. As illustrated in FIG. 9, CPU 811 may be communicatively coupled to RAM 812, ROM 813, storage 814, database 815, I/O devices 816, and interface 817. CPU 811 may be configured to execute sequences of computer program instructions to perform various processes, which will be described in detail below. The computer program instructions may be loaded into RAM 812 for execution by CPU 811.

RAM 812 and ROM 813 may each include one or more devices for storing information associated with an operation of processing system 810 and/or CPU 811. For example, ROM 813 may include a memory device configured to access and store information associated with processing system 810, including information for identifying, initializing, and monitoring the operation of one or more components and subsystems of processing system 810. RAM 812 may include a memory device for storing data associated with one or more operations of CPU 811. For example, ROM 813 may load instructions into RAM 812 for execution by CPU 811.

Storage 814 may include any type of mass storage device configured to store information that CPU 811 may need to perform processes consistent with the disclosed embodiments. For example, storage 814 may include one or more magnetic and/or optical disk devices, such as hard drives, CD-ROMs, DVD-ROMs, or any other type of mass media device. Alternatively or additionally, storage 814 may include flash memory mass media storage or other semiconductor-based storage medium.

Database 815 may include one or more software and/or hardware components that cooperate to store, organize, sort, filter, and/or arrange data used by processing system 810 and/or CPU 811. For example, database 815 may include historical data such as, for example, stored TFS cue estimate or exemplary noise and bandwidth signals that may be used for training source separation algorithms. CPU 811 may access the information stored in database 815 to provide a user with the ability to tune the cochlear implant algorithm to aid in the proper segregation between noise and background signals. With user feedback, CPU 811 may also analyze current and previous speech recognition data in order to assist in tuning signal processing and noise reduction schemes to increase the performance of the implant.

I/O devices 816 may include one or more components configured to communicate information with a user associated with the auditory prosthetic device. For example, I/O devices may include a micro-USB or other serial port for allowing a technician to test the functionality of the auditory prosthetic device when not in use. I/O devices 816 may also include input ports for connecting external audio signal detection components, such as microphone 111a for receiving audio signals for processing by the signal processing system. I/O devices 816 may also include interfaces for attaching individual electrodes 110 and or electrode arrays 112 for delivering electric stimulation to the auditory nerve of a user.

Interface 817 may include one or more components configured to transmit and receive data via a communication network, such as the Internet, a local area network, a workstation peer-to-peer network, a direct link network, a wireless network, or any other suitable communication platform. For example, interface 817 may include one or more modulators, demodulators, multiplexers, demultiplexers, network communication devices, wireless devices, antennas, modems, and any other type of device configured to enable data communication via a communication network. According to one embodiment, interface 817 may be coupled to or include wireless communication devices, such as a module or modules configured to transmit information wirelessly using Wi-Fi or Bluetooth wireless protocols.

It will be apparent to those skilled in the art that various modifications and variations can be made to the disclosed systems and methods for multi-carrier processing in auditory prosthetic devices. Other embodiments of the present disclosure will be apparent to those skilled in the art from consideration of the specification and practice of the present disclosure. It is intended that the specification and examples be considered as exemplary only, with a true scope of the present disclosure being indicated by the following claims and their equivalents.

What is claimed is:

1. A method for multi-carrier processing in an auditory prosthetic device, comprising:
   receiving an audio signal comprising multiple signals, each signal produced by an independent source;
   identifying at least a first signal and a second signal in the received audio signal;
   dividing the first signal into one or more frequency bands;
   dividing the second signal into the one or more frequency bands, wherein the one or more frequency bands include a matching frequency band that is the same for both the first and second signals;
   generating a first carrier signal and a second carrier signal for the matching frequency band;
   dynamically adjusting an amplitude of the first carrier signal based on the first signal in the matching frequency band or a signal envelope associated with the first signal in the matching frequency band;
   dynamically adjusting an amplitude of the second carrier signal based on the second signal in the matching frequency band or a signal envelope associated with the second signal in the matching frequency band;
   adding the amplitude-adjusted first and second carrier signals associated with the matching frequency band; and
   delivering the summed amplitude-adjusted first and second carrier signals associated with the matching frequency band to at least one electrode associated with an auditory prosthetic device.

2. The method of claim 1, wherein the first signal includes a target signal and the second signal includes one or more background signals.

3. The method of claim 2, wherein the target signal corresponds to target speech in the received audio signal and the one or more background signals correspond to a respective noise source in the received audio signal.

4. The method of claim 1, wherein the audio signal includes music, wherein the first signal is associated with a first target source in the music and wherein the second signal is associated with a second target source in the music.

5. The method of claim 1, wherein identifying the first signal includes isolating the first signal using noise reduction or signal separation, and wherein identifying the second signal includes:
   determining an amplitude-inversed waveform associated with the first signal; and
   removing the amplitude-inversed waveform from the received audio signal.

6. The method of claim 1, wherein the second signal includes a plurality of signals, and further wherein dynamically adjusting the amplitude of the second carrier signal includes modulating a respective carrier signal with a respective one of the plurality of signals.

7. The method of claim 1, wherein a frequency associated with the first carrier signal includes an estimated fundamental frequency of the first signal, or a frequency associated with the second carrier signal includes an estimated fundamental frequency of the second signal.

8. The method of claim 1, wherein the frequency associated with at least one of the first carrier signal or the second carrier signal is between about 100 Hz and 1000 Hz, and wherein the second carrier frequency is separated from the first carrier frequency by at least about 20 Hz.

9. A processor-implemented method for delivering temporal fine structure information to an output of an auditory prosthetic device, comprising:
   receiving an audio signal comprising multiple signals, each signal produced by an independent source;
   identifying at least a first signal and a second signal in the received audio signal;
   dividing the first signal into one or more frequency bands;
   dividing the second signal into the one or more frequency bands, wherein the one or more frequency bands include a matching frequency band that is the same for both the first and second signals;
   estimating a fundamental frequency of the first signal;
   dynamically adjusting an amplitude of a first carrier signal based on the first signal in the matching frequency band or a signal envelope associated with the first signal in the matching frequency band, wherein the first carrier signal includes the fundamental frequency of the first signal;
   estimating a fundamental frequency of the second signal;
   dynamically adjusting an amplitude of a second carrier signal based on the second signal in the matching frequency band or a signal envelope associated with the second signal in the matching frequency band, wherein the second carrier signal includes the fundamental frequency of the second signal;
   adding the amplitude-adjusted first and second carrier signals associated with the matching frequency band; and
   delivering the summed amplitude-adjusted first and second carrier signals associated with the matching frequency band to at least one stimulator associated with an auditory prosthetic device.

10. The processor-implemented method of claim 9, wherein the first signal includes a target signal and the second signal includes one or more background signals.

11. The processor-implemented method of claim 9, wherein the audio signal includes music, wherein the first signal is associated with a first target source in the music and wherein the second signal is associated with a second target source in the music.

12. The processor-implemented method of claim 9, wherein identifying the first signal includes isolating the first signal using noise reduction or signal separation, and wherein identifying the second signal includes:
   determining an amplitude-inversed waveform associated with the first signal; and
   removing the amplitude-inversed waveform from the received audio signal.

13. The processor-implemented method of claim 9, wherein the second signal includes a plurality of signals, and further wherein dynamically adjusting the amplitude of the second carrier signal includes modulating a respective carrier signal with a respective one of the plurality of signals.

14. The processor-implemented method of claim 9, wherein a frequency associated with the first carrier signal includes the estimated fundamental frequency of the first signal, or a frequency associated with the second carrier signal includes the estimated fundamental frequency of the second signal.

15. The processor-implemented method of claim 9, wherein the frequency associated with at least one of the first carrier signal or the second carrier signal is between about 100 Hz and 1000 Hz, and wherein the second carrier frequency is separated from the first carrier frequency by at least about 20 Hz.

16. An auditory prosthetic device, comprising:
a microphone for detecting an audio signal;
a stimulator array adapted for implantation proximate a neural structure in a patient and configured to deliver stimulation to the neural structure;
a processor communicatively coupled to the microphone and the stimulator array, the processor configured to:
identify at least a first signal and a second signal in the detected audio signal;
divide the first signal into one or more frequency bands;
divide the second signal into the one or more frequency bands, wherein the one or more frequency bands include a matching frequency band that is the same for both the first and second signals;
dynamically adjust an amplitude of a first carrier signal based on the first signal in the matching frequency band or a signal envelope associated with the first signal in the frequency band;
dynamically adjust an amplitude of a second carrier signal based on the second signal in the matching frequency band or a signal envelope associated with the second signal in the matching frequency band;
add the amplitude-adjusted first and second carrier signals associated with the matching frequency band; and
deliver the summed amplitude-adjusted first and second carrier signals associated with the matching frequency band to the stimulator array.

17. The auditory prosthetic device of claim 16, wherein the first signal includes a target signal and the second signal includes at least one background signal.

18. The auditory prosthetic device of claim 16, wherein the second signal includes a plurality of signals, and further wherein dynamically adjusting the amplitude of the second carrier signal includes modulating a respective carrier signal with a respective one of the plurality of signals.

19. The auditory prosthetic device of claim 16, wherein a frequency associated with the first carrier signal includes an estimated fundamental frequency of the first signal and a frequency associated with the second carrier signal includes an estimated fundamental frequency of the second signal.

20. The auditory prosthetic device of claim 16, wherein the simulator array includes at least one of a device for generating optical or light stimulation or an electrode array for generating electromagnetic pulse energy.

* * * * *